(12) United States Patent
Dreisbach et al.

(10) Patent No.: US 7,057,061 B2
(45) Date of Patent: Jun. 6, 2006

(54) CHIRAL MONOPHOSPHORUS COMPOUNDS

(75) Inventors: Claus Dreisbach, Leichlingen (DE); Benjamin Meseguer, Tarragona (ES); Thomas Prinz, Leverkusen (DE); Ulrich Scholz, Mühlheim (DE); Hans-Christian Militzer, Odenthal (DE); Friederike Agel, Aachen (DE); Birgit Drießen-Hölscher, Aachen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 99 days.

(21) Appl. No.: 10/256,700

(22) Filed: Sep. 27, 2002

(65) Prior Publication Data
US 2003/0119664 A1 Jun. 26, 2003

(30) Foreign Application Priority Data
Oct. 2, 2001 (DE) ............................... 101 48 551

(51) Int. Cl.
C07F 9/655 (2006.01)
(52) U.S. Cl. .......................................... 558/85; 558/70
(58) Field of Classification Search ................. 558/70, 558/72, 85
See application file for complete search history.

(56) References Cited

U.S. PATENT DOCUMENTS

| 3,689,602 | A | * | 9/1972 | Ismail et al. ................... 558/85 |
| 4,288,391 | A | * | 9/1981 | Spivack ........................ 558/78 |
| 4,414,345 | A | * | 11/1983 | Rasberger .................... 524/108 |
| 4,599,206 | A | | 7/1986 | Billig et al. ................... 558/85 |
| 4,717,775 | A | * | 1/1988 | Billig et al. ................. 568/454 |
| 4,835,299 | A | * | 5/1989 | Maher et al. ................. 558/85 |
| 5,932,772 | A | * | 8/1999 | Argyropoulos et al. ...... 568/454 |
| 2003/0171608 | A1 | | 9/2003 | Reezt et al. ................. 558/348 |

FOREIGN PATENT DOCUMENTS

DE 10027505 A1 * 12/2001
WO 99 59721 A 11/1999

OTHER PUBLICATIONS

CA:119:159872 abs of WO 930839 Mar. 1993.*
CA:107:7392 abs of WO 213639 Mar. 1987.*
CA:68:12597 abs of Zhurnal Obshchei Khimii by Verizhnikov et al 37(6) pp. 1355-1358 1967.*
CA:99:105356 abs of Phosphorus and Sulfur and the Related Elements by Pastor et al 15(2) pp.253-256 1983.*
CA:116:174252 abs of Inorganic Chemistry by Hans et al 31(7) pp. 1279-1285 1992.*
CA:75:130242 abs of Zhurnal Khimii by Verizhnikov abstract No. 19S210 1970.*
CA:103:71388 abs of Phosphorus and Sulfur and the Related Elements by Abdou et al 22(1) pp. 99-107 1985.*
Whiteker G. T. et al.: "Direct NMR observation of atropisomerism of a bisphosphite Dibenzo(d,f)(1,3,2)dioxaphosphepin moeity" Journal of The Chemical Society, Chemical Communications., Nr. 17, 1995, Seiten 1805-1806, XPO02249645 Chemical Society. Letchworth., GB ISSN: 0022-4936 * Verbindung der Formel 2 und deren Herstellung *.
Van Strijdonck G. P. F. et al.: "Fast Palladium catalyzed arylation of alkenes using bulky monodentate phosphorus ligands" European Journal of Inorganic Chemistry., Nr. 7, 1999, XPO02249646 Wiley-Vch Verlag, Weinheim., DE ISSN: 1434-1948 * Verbindungen 1a, 1b and 3b *.
Alexakis A. et al.: "Novel biphenol phosphoramidite ligands for the enantioselective Copper catalyzed conjugate addition of dialkyl zincs" Synlett. , Nr. 9,—Sep. 2001 Seiten 1375-1378, XPO02249647 Thieme Verlag, Stuttgart., DE ISSN: 0936-5214 * Verbindungen L4, L4', L5 und L6 * .
Bartels B. et al.: "Ir-catalyzed allylic substitution: mechanistic aspects and asymmetric synthesis with phosphorus amidites as ligands" Journal of Chemical Society, Chemical Communications., Nr. 8, Apr. 21, 1999, Seiten 741-742, XPO02249648 Chemical Society. Letchworth., GB ISSN: 0022-4936 * Verbindung 7 *.
Reetz M T et al: "New Diphosphite Ligands 17,8 for Catalytic Asymmetric Hydrogenation: The Crucial Role of Conformationally Enantiomeric Diols" Angewandte Chemie. International Edition, Verlag Chemie. Weinheim, DE, Bd. 38, Nr. 1/2, 1999, Seiten 179-181, XPO01069475 ISSN: 0570-08333 * Tabelle 1 *.
Buisman G J H et al: "Rhodium Catalysed Asymmetric Hydroformylation with Diphosphite Ligands based on Sugar Backbones" Tetrahedron: Asymmetry, Elsevier Science Publishers, Amsterdam, NL, Bd. 6, Nr. 3, (Mar. 1, 1995), Seiten 719-738, XPO04048415 ISSN: 0957-4166 * Verbindungen der Formel 1a, und 1b, 1c *.
Van Rooy A. et al.: "Phosphoramidites: novel modifying ligands in rhodium catalyzed hydroformylation" Recueil Des Travaux Chimiques Des Pays-Bas., Bd. 115, Nr. 11-12, 1996, Seiten 492-498, XPO08020304 Elsevier Science Publishers. Amsterdam., NL ISSN: 0165-0513 * Verbindungen der Formeln 2 und 3 *.
Jiang Y et al: "Asymmetric hydroformylation catalyzed by rhodium(l) complexes of novel chiral spiro ligands" Journal of Organometallic Chemistry, Elsevier-Sequoia S.A. Lausanne, CH, Bd. 586, Nr. 2, Sep. 5, 1999, Seiten 159-165, XPO04183023 ISSN: 0022-328X * Verbindungen der Formeln 4a und 4b*.

(Continued)

Primary Examiner—Rosalynd Keys
(74) Attorney, Agent, or Firm—Jennifer R. Seng

(57) ABSTRACT

The present invention relates to catalysts comprising chiral monophosphorus compounds and their use, the chiral monophosphorus compounds themselves and also their precursors.

1 Claim, No Drawings

OTHER PUBLICATIONS

Reetz M. T. et al: "Highly enantioselective Rh-catalyzed hydrogenation reactions based on chiral monophosphite ligands" Angewandte Chemie. International Edition, Verlag Chemie. Weinheim, DE, Bd. 39, Nr. 21, Nov. 3, 2000, Seiten 3889-3890, XPO02180131 ISSN: 0570-0833 * das ganze Dokument* .

Claver C. et al.: "Biarylphosphonites: a class of monodentate phosphorus(III) ligands that outperform their chelating analogues in asymmetric hydrogenation catalysts" Chemical Communications., Nr. 11, 7. Jun. 7, 2000, Seiten 961-962, XPO02249649 Royal Society of Chemistry., GB ISSN: 1359-7345 * das ganze Dokument* .

Van Den Berg M. et al.: "Highly enantioselective Rhodium catalyzed hydrogenation with monodentate ligands" Journal of the American Chemical Society., Bd. 122, Nr. 46, Nov. 22. 2000, Seiten 11539-11540, XPO02249650 American Chemical Society, Washington, DC., US ISSN: 0002-7863 * das ganze Dokument* .

Van den Berg, M. et al., Supporting Information for "Highly Enatioselective Rhodium-Catalyzed Hydrogenation and Monodenate Ligands." J. Am. Chem. Society, 2000, 122, 11539-11540.

Alexakis, A., "Asymmetric conjugate addition of diethyl zinc to encones with tartrate chiral phosphite ligands." Tetrahedron: Asymmetric, vol. 8, No. 19, pp. 3193-3196, 1997.

Huttenloch, O., et al., "Chiral Bicycle Phosphoramidities—A New Class of Ligands for Asymmetric Catalysis." Chem. Eur. 2000, 6, No. 3, 671-675.

Chen, W., et al, "Enantioselective hydrogenation with inexspensive, easily available monodenate phosphite ligands." Tetrahedron Letters 42 (2001) 2897-2899.

* cited by examiner

CHIRAL MONOPHOSPHORUS COMPOUNDS

BACKGROUND OF THE INVENTION

1. Field of the Invention

The present invention relates to catalysts comprising chiral monophosphorus compounds and their use, the chiral monophosphorus compounds themselves and also their precursors. For the purposes of the invention, chiral monophosphorus compounds are, in particular, chiral monophosphites, monophosphoramidites and monophosphonites.

2. Brief Description of the Prior Art

It is already known that chiral monophosphites or their transition metal complexes can be used for asymmetric syntheses (cf. A. Alexakis, Tetrahedron Asymmetry, 1997, 8, 3193–3196; C. Claver et al., Chem. Commun., 2000, 2383–2384; W. Chen, J. Xiao, Tetrahedron Letters, 42, 2001, 2897–2899; M. Reetz, G. Mehler, Angew. Chem., 2000, 112, 4047–4049). The use of chiral monophosphoramidites or their transition metal complexes in asymmetric syntheses is known, for example from van den Berg et al., J. Am. Chem. Soc., 2000, 122, 11539–11540, and H. Waldmann, Chem. Eur. J. 2000, 6, 671–675, and the use of chiral monophosphonites is known from C. Claver et al., Chem. Commun., 2000, 961–962.

However, all chiral ligands known hitherto are derived from the basic framework of 2,2'-dihydroxy-1,1'-binaphthyl or other polycyclic dihydroxybisaryls. The disadvantage of such ligands is that only limited substitution opportunities are available for varying the electronic and steric properties. Use in various asymmetric reaction types and applicability to many substrates does, however, make a broad range of possible substitutions desirable.

Furthermore, there is a need to develop catalysts which, particularly when used in asymmetric hydrogenations, give not only a high enantioselectivity but also high conversions and mild to moderate reaction conditions.

SUMMARY OF THE INVENTION

It has now surprisingly been found that chiral monophosphorus compounds of the general formula (I) or catalysts based on these are particularly suitable for asymmetric syntheses,

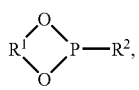

(I)

where
  $R^1$ is an unsubstituted or substituted 1,1'-biphenyl-2,2'-diyl radical and $R^2$ is a radical selected from the group consisting of substituted or unsubstituted alkyl, substituted or unsubstituted aryl, substituted or unsubstituted alkoxy, substituted or unsubstituted aryloxy and tertiary amino.
  $R^2$ is preferably substituted or unsubstituted alkoxy or substituted or unsubstituted aryloxy or tertiary amino, particularly preferably substituted or unsubstituted alkoxy or substituted or unsubstituted aryloxy.

DETAILED DESCRIPTION OF THE INVENTION

The following is a detailed description of the invention with particular reference to its preferred elements. Unsubstituted or substituted alkyl is, by way of example and preferably, an unbranched, branched, cyclic or acyclic $C_1$–$C_{18}$-alkyl radical which is either unsubstituted or at least partially substituted by fluorine, chlorine, bromine, oxo, hydroxy, unsubstituted or substituted aryl, $C_1$–$C_6$-alkoxy such as methoxy, ethoxy, isopropoxy or n-propoxy, n-butoxy, or tert-butoxy, primary, secondary or tertiary amino, cyano or carboxyl groups or derivatives thereof. Examples of derivatives of carboxyl groups are esters, amides and salts.

Unsubstituted or substituted alkyl is particularly preferably a branched, cyclic or acyclic $C_3$–$C_{12}$-alkyl radical which is either unsubstituted or at least partially substituted by fluorine, oxo, hydroxy, methoxy, ethoxy, phenyl, 2-methoxyphenyl, 2-pyridyl, 3-pyridyl, 4-pyridyl, amino, dimethylamino, diethylamino, diisopropylamino, cyano or carboxyl groups, their salts such as sodium or potassium salts or their esters such as methyl or ethyl esters or their amides such as dimethylamides or diethylamides.

Unsubstituted or substituted alkyl is very particularly preferably isopropyl, tert-butyl, cyclohexyl, 1-butyl, 2-butyl, 2-ethylhex-1-yl, benzyl, 2-methoxybenzyl, 2-pyridylmethyl, 1-phenylethyl.

Unsubstituted or substituted alkoxy is, by way of example and preferably, an unbranched, branched, cyclic or acyclic $C_1$–$C_{18}$-alkoxy radical which is either unsubstituted or at least partially substituted by fluorine, chlorine, bromine, oxo, free or protected hydroxy, $C_1$–$C_6$-alkoxy such as methoxy, ethoxy, isopropoxy or n-propoxy, n-butoxy or tert-butoxy, substituted or unsubstituted $C_6$–$C_{10}$-aryl such as phenyl or 2-pyridyl, primary, secondary or tertiary amino, cyano or carboxyl groups or derivatives thereof.

Unsubstituted or substituted alkoxy is particularly preferably an unbranched, branched, cyclic or acyclic $C_2$–$C_{12}$-alkoxy radical which is either unsubstituted or at least partially substituted by fluorine, chlorine, free or protected hydroxy, substituted or unsubstituted phenyl, 2-pyridyl, $C_1$–$C_6$-alkoxy such as methoxy, ethoxy, isopropoxy or n-propoxy, n-butoxy or tert-butoxy, $C_1$–$C_6$-dialkylamino, $C_1$–$C_6$-alkylcarbonylamino, benzoylamino, 4-methylphenylsulphonylamino, imidazolyl, phthalimidyl, $C_1$–$C_6$-alkyloxycarbonyl, $C_1$–$C_4$-dialkylaminocarbonyl.

Unsubstituted or substituted alkoxy is very particularly preferably an unbranched, branched, cyclic or acyclic $C_2$–$C_6$-alkoxy radical which is either unsubstituted or at least partially substituted by fluorine, chlorine, free or protected hydroxy, monosubstituted or disubstituted or unsubstituted phenyl, 2-pyridinyl, $C_1$–$C_4$-dialkylamino, $C_1$–$C_4$-alkylcarbonylamino, benzoylamino, 4-methylphenylsulphonylamino, imidazolyl, phthalimidyl, $C_1$–$C_4$-alkyloxycarbonyl, $C_1$–$C_4$-dialkylaminocarbonyl, $C_1$–$C_4$-alkoxy such as methoxy, ethoxy, isopropoxy or n-propoxy, n-butoxy or tert-butoxy.

Unsubstituted or substituted alkoxy is even more preferably methoxy, ethoxy, isopropoxy, cyclohexyloxy, phenoxy, (R)-1-phenylethoxy or (S)-1-phenylethoxy.

Substituted or unsubstituted aryl is, by way of example and preferably, a carbocyclic aromatic radical having from 6 to 18 framework carbon atoms or a heteroaromatic radical having from 5 to 18 framework carbon atoms in which no, one, two or three framework carbon atoms per ring, but at least one framework carbon atom in the total molecule, can be replaced by heteroatoms selected from the group consisting of nitrogen, sulphur and oxygen. Furthermore, the carbocyclic aromatic radicals or heteroaromatic radicals can be substituted by up to five identical or different substituents per ring selected from the group consisting of free or protected hydroxy, iodine, bromine, chlorine, fluorine, cyano, free or protected formyl, $C_1$–$C_{12}$-alkyl such as methyl, ethyl, n-propyl, isopropyl, n-butyl, tert-butyl, cyclohexyl, n-hexyl, n-octyl or isooctyl, $C_6$–$C_{12}$-aryl such as phenyl, tri($C_1$–$C_6$-alkyl)siloxyl such as trimethylsiloxyl, triethylsiloxyl or tri-n-butylsiloxyl and radicals of the general formula (II),

A—B—D—E (II), where, independently of one another,
A is absent or is a $C_1$–$C_8$-alkylene radical such as methylene, 1,2-ethylene, 1,1-ethylene, 1,3-propylene, 1,2-propylene, 1,4-butylene or 2,3-butylene and
B is absent or is oxygen, sulphur or $NR^3$,
  where
    $R^3$ is hydrogen, $C_1$–$C_{16}$-alkyl such as methyl, ethyl, n-propyl, isopropyl, n-butyl, tert-butyl, cyclohexyl, n-hexyl, n-octyl or isooctyl or $C_6$–$C_{10}$-aryl such as phenyl or 2-, 3- or 4-tolyl and
D is a carbonyl group and
E is $R^4$, $OR^4$, $NHR^5$ or $N(R^5R^6)_2$,
  where
    $R^4$ is $C_1$–$C_{12}$-alkyl, $C_6$–$C_{10}$-aryl and
    $R^5$ and $R^6$ are each, independently of one another, $C_1$–$C_8$-alkyl or $C_6$–$C_{10}$-aryl or the $N(R^5R^6)_2$ moiety is a cyclic amino radical, and radicals of the general formulae (IIIa) and (IIIb)

A—E (IIIa)

A—COX (IIIb)

where A and E are as defined above and X is OH, $NH_2$ or OM, where M can be an alkali metal ion, half an equivalent of an alkaline earth metal ion, an ammonium ion or an organic ammonium ion.

Examples of carbocyclic aromatic radicals having from 6 to 18 framework carbon atoms are phenyl, naphthyl, phenanthrenyl, anthracenyl or fluorenyl, heteroaromatic radicals having from 5 to 18 framework carbon atoms in which no, one, two or three framework carbon atoms per ring, but at least one framework carbon atom in the total molecule, can be replaced by heteroatoms selected from the group consisting of nitrogen, sulphur and oxygen are, for example, pyridinyl, oxazolyl, thienyl, benzofuranyl, benzothienyl, dibenzofuranyl, dibenzothienyl, furanyl, indolyl, pyridazinyl, pyrazinyl, pyrimidinyl, triazolyl or quinolinyl.

For the purposes of the invention, protected formyl is a formyl radical which has been protected by conversion into an aminal, acetal or a mixed aminal-acetal, with the aminals, acetals and mixed aminal-acetals being able to be acyclic or cyclic.

For the purposes of the invention, protected hydroxy is a hydroxy radical which has been protected by conversion into an acetal, carbonate, carbamate or carboxylate. Examples are conversion into a tetrahydropyranyl adduct, into a benzyloxycarbonyl, allyloxycarbonyl or tert-butyloxycarbonyl derivative.

Substituted or unsubstituted aryloxy is, by way of example and preferably, a radical of the formula (IV)

—O—Ar (IV)

where Ar has the same widest meaning as indicated above for substituted or unsubstituted aryl.

Unsubstituted or substituted aryloxy is particularly preferably a radical of the general formula (IV), in which Ar is phenyl, naphthyl, anthracenyl, phenanthrenyl, pyridinyl, pyrazinyl, pyridazinyl or pyrimidinyl which can be substituted by no, one, two or three further substituents per ring selected from the group consisting of free or protected hydroxy, bromine, chlorine, fluorine, cyano, methyl, ethyl, n-propyl, isopropyl, n-butyl, n-pentyl, n-hexyl, phenyl, benzyl, $C_1$–$C_{12}$-perfluoroalkyl such as trifluoromethyl, pentafluoroethyl, and substituents of the general formulae (II) and (IIIa) and (IIIb) in which, in each case independently of one another, A is absent or is methylene,
B is absent or is oxygen or $NR^3$,
  where
    $R^3$ is hydrogen, methyl or ethyl and
D is a carbonyl group and
E is $R^4$, $OR^4$, $NHR^5$ or $NR^5R^6$,
  where
    $R^4$ is methyl, ethyl, n-propyl, isopropyl, n-butyl, tert-butyl, benzyl, 2-hydroxyethyl, trifluoromethyl or phenyl and
    $R^5$ and $R^6$ are each, independently of one another, methyl, ethyl, n-propyl, isopropyl, n-butyl, benzyl, 2-hydroxyethyl or phenyl or
    the $NR^5R^6$ moiety is morpholinyl, piperidinyl or pyrolidinyl and
X is OH, $NH_2$, or OM, where M is a sodium, potassium or ammonium ion.

Unsubstituted or substituted aryloxy is very particularly preferably a radical of the general formula (IV), in which Ar is phenyl which is substituted by no, one or two further substituents selected from the group consisting of fluorine, chlorine, cyano, methoxy, methyl, ethyl, phenyl, trifluoromethyl, and radicals of the general formulae (II) and (IIIa) and (IIIb) in which A and B are absent and
D is a carbonyl group and
E is $R^4$ or $OR^4$,
  where
    $R^4$ is methyl, ethyl or phenyl.

Unsubstituted or substituted aryloxy is even more preferably phenoxy, 2,4-dimethylphenoxy, 3,5-dimethylphenoxy, 3,5-bis(trifluoromethyl)-phenoxy, 4-methylphenoxy, 3-methylphenoxy, 3-methoxyphenoxy, 4-methoxyphenoxy, 2-methoxyphenoxy, 2-methylphenoxy, 2,4-dichlorophenoxy, 2-ethoxycarbonylphenyl, 2-methoxycarbonyl, 2-acetylphenyl, 4-acetylphenyl or 2,6-dimethylphenoxy.

Tertiary amino is, for example, alkylarylamino, dialkylamino or diarylamino, preferably dialkylamino or diarylamino. Cyclic amino radicals are also encompassed by the invention.

Preferred examples of tertiary amino are di(substituted or unsubstituted ($C_1$–$C_{12}$-alkyl)amino such as dimethylamino, diethylamino, diisopropylamino, di-n-butylamino, di-(R)-phenylethylamino, di-(S)-phenylethylamino, dibenzylamino and di(substituted or unsubstituted $C_6$-$C_{10}$-aryl)amino, such as diphenylamino, di-(p-tolyl)amino or cyclic amino radicals such as R,R-dimethylpyrrolidino, S,S-dimethylpyrrolidino, morpholino, piperidino, tetramethylpiperidino.

$R^1$ is, by way of example and preferably, an unsubstituted or substituted 1,1'-biphenyl-2,2'-diyl radical of the general formula (VI),

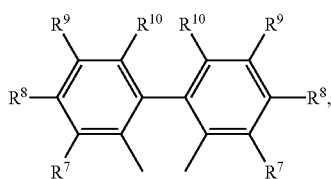

where the radicals $R^7$, $R^8$, $R^9$ and $R^{10}$ are each selected independently from the group consisting of fluorine, chlorine, bromine, unsubstituted or substituted protected hydroxy, unsubstituted or substituted $C_1$–$C_6$-alkyl, unsubstituted or substituted $C_1$–$C_6$-alkoxy, unsubstituted or substituted $C_1$–$C_6$-alkylthio, cyano, free or protected formyl, unsubstituted or substituted $C_6$–$C_{12}$-aryl, tri($C_1$–$C_6$-alkyl) siloxyl and radicals of the general formula (II),

A—B—D—E    (II), where, independently of one another,
  A is absent or is a $C_1$–$C_8$-alkylene radical and
  B is absent or is oxygen, sulphur or $NR^3$,
    where
    $R^3$ is hydrogen, $C_1$–$C_{16}$-alkyl or $C_6$–$C_{10}$-aryl and
    D is a carbonyl group and
    E is $R^4$, $OR^4$, $NHR^5$ or $NR^5R^6$,
      where
      $R^4$ is $C_1$–$C_{12}$-alkyl or $C_6$–$C_{10}$-aryl and
      $R^5$ and $R^6$ are each, independently of one another, $C_1$–$C_8$alkyl or $C_6$–$C_{10}$-aryl or the $NR^5R^6$ moiety is a cyclic amino radical, and radicals of the general formulae (IIIa) and (IIIb) with the widest meaning indicated above.

The two radicals $R^{10}$ together can also be bridging. The invention also encompasses cases in which the two radicals $R^{10}$ are each chiral or are together chiral and bridging.

Furthermore, the two radicals can also form a nonaromatic ring.

$R^1$ is particularly preferably an unsubstituted or substituted 1,1'-biphenyl-2,2'-diyl radical of the general formula (VI) in which the radicals $R^7$, $R^8$, $R^9$ and $R^{10}$ are each selected independently from the group consisting of fluorine, chlorine, bromine, free or protected hydroxy, unsubstituted or substituted $C_1$–$C_4$-alkyl, unsubstituted or substituted $C_1$–$C_4$-alkoxy, unsubstituted or substituted $C_1$–$C_4$-alkylthio, cyano, $C_6$-aryl, tri($C_1$–$C_4$-alkyl)siloxyl and radicals of the general formula (II),

A—B—D—E    (II)

where, independently of one another,
  A is absent or is a $C_1$–$C_4$-alkylene radical and
  B is absent or is oxygen or $NR^3$,
    where $R^3$ is hydrogen, $C_1$–$C_6$-alkyl or $C_6$–$C_{10}$aryl and
    D is a carbonyl group and
    E is $R^4$, $OR^4$, $NHR^5$ or $NR^5R^6$,
    where $R^4$ is $C_1$–$C_6$-alkyl or $C_6$–$C_{10}$ aryl and
    $R^5$ and $R^6$ are each, independently of one another, $C_1$–$C_4$-alkyl or $C_6$-aryl or the $NR^5R^6$ moiety is a cyclic amino radical, and radicals of the general formulae (IIIa) and (IIIb) with the widest meaning indicated above.

The two radicals $R^{10}$ can together also be bridging. Bridges formed in this way are, preferably and by way of example, bridges of the formula (VII)

—O—$G^1$—K—$G^2$—O—    (VII)

where $G^1$ and $G^2$ can each, independently of one another, either be absent or be a carbonyl group or a carbonylamino group,
K can be an unsubstituted or substituted $C_2$–$C_6$-alkylene chain.

$R^1$ is very particularly preferably an unsubstituted or substituted 1,1'-biphenyl-2,2'-diyl radical of the general formula (VI) in which the radicals $R^7$, $R^8$, $R^9$ and $R^{10}$ are each selected independently from the group consisting of fluorine, chlorine, bromine, free or protected hydroxy, unsubstituted or substituted $C_1$–$C_4$-alkyl, unsubstituted or substituted $C_1$–$C_4$-alkoxy and radicals of the general formula (II),

A—B—D—E    (II)

in which, independently of one another,
  A is absent and
  B is absent or is oxygen,
  and
  D is a carbonyl group and
  E is $R^4$, $OR^4$, $NHR^5$ or $NR^5R^6$,
  where $R^4$ is $C_1$–$C_4$-alkyl or $C_6$–$C_{10}$-aryl and
  $R^5$ and $R^6$ are each, independently of one another, $C_1$–$C_4$-alkyl or the $NR^5R^6$ moiety is a cyclic amino radical,
  and radicals of the general formulae (IIIa) and (IIIb) with the widest meaning indicated above or the two radicals $R^{10}$ are bridges of the general formula (VII) in which G can either be absent or be a carbonyl group or a carbonyl amino group and
K is an unsubstituted or substituted $C_2$–$C_4$-alkylene chain.

$R^1$ is even more preferably one of the following radicals:

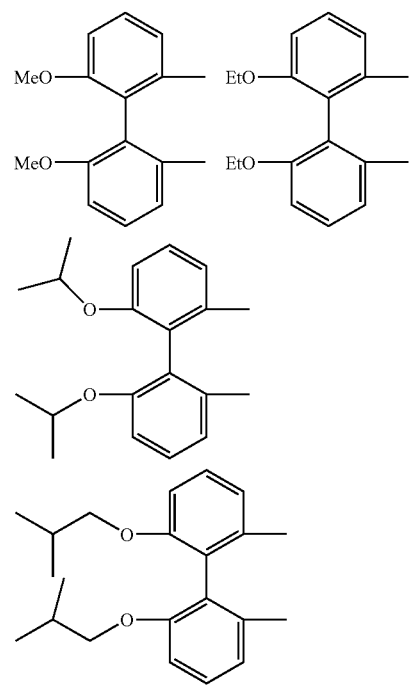

-continued
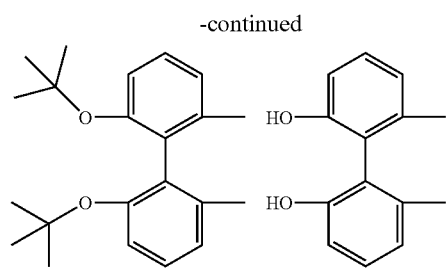
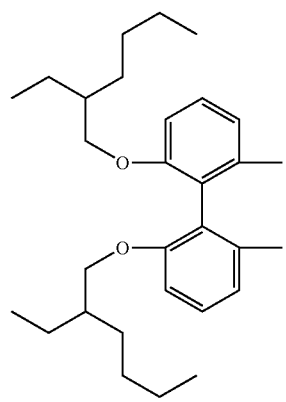
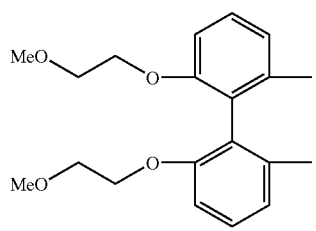
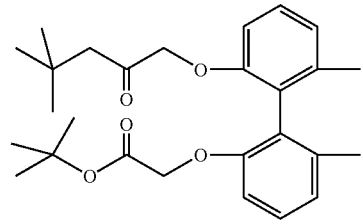
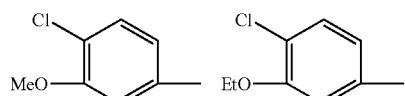
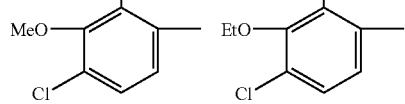
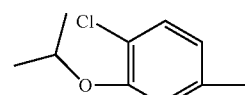
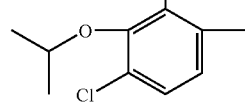
-continued
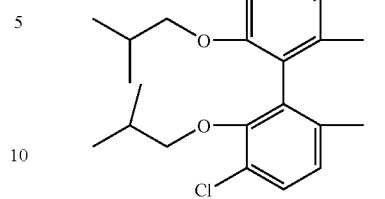
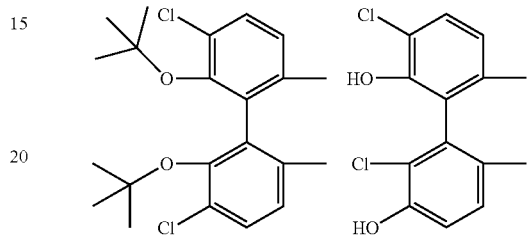
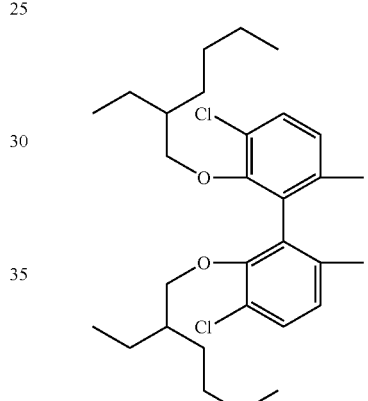
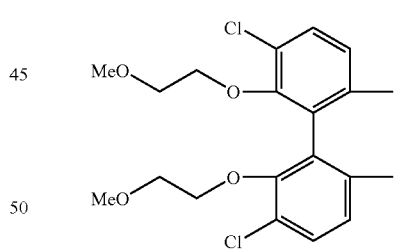
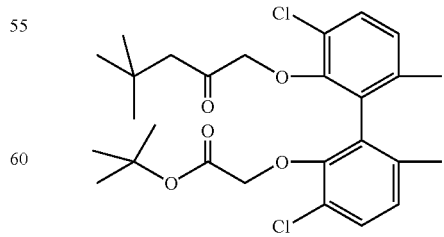
or a radical of the general formula (VIII)

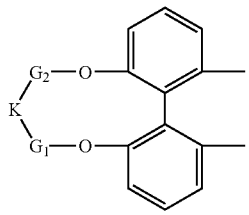
(VIII)
where G$^1$—K—G$^2$ together represent (R)-1,2-propanediyl, (S,S)-1,2-cyclohexanediyl, (R,R)-1,2-cyclohexanediyl, 1,2-ethanediyl, 1,3-propanediyl, 1,4-butanediyl or 1,4-dioxobutanediyl or one of the following radicals:
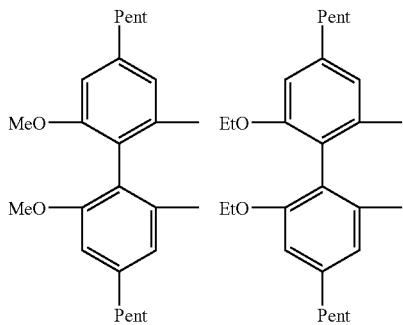
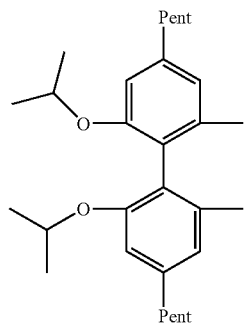
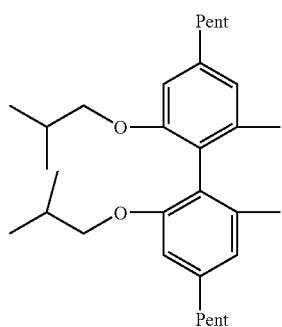
-continued
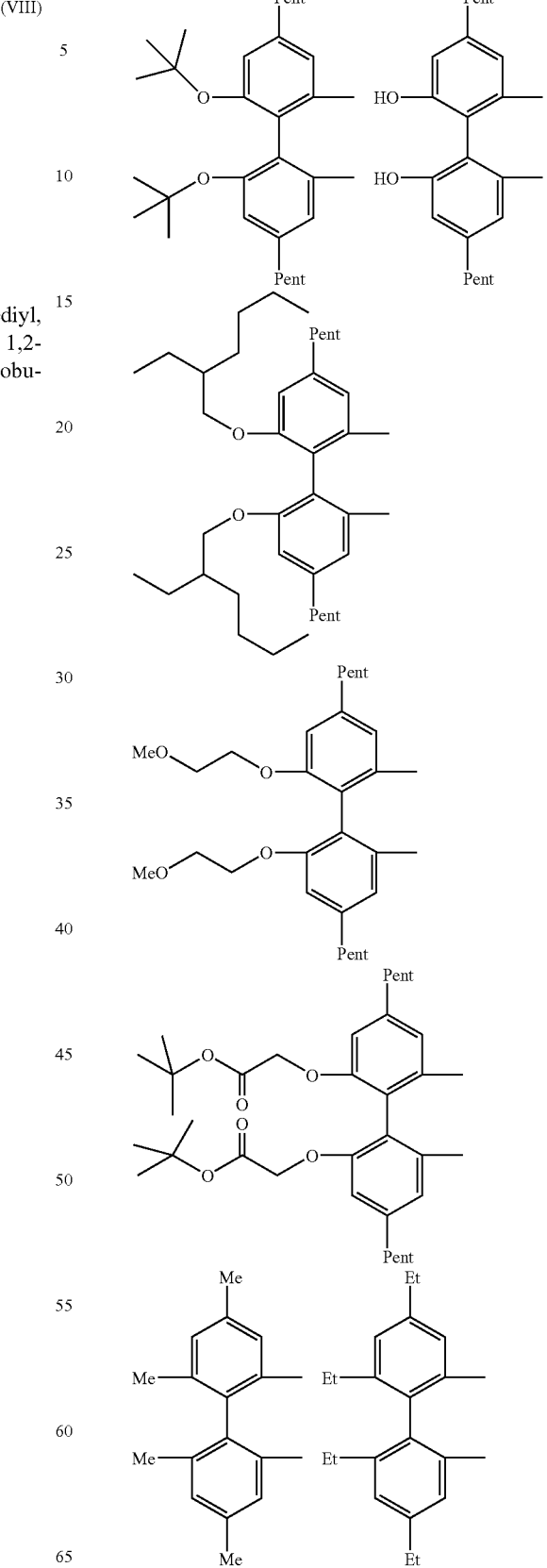

-continued

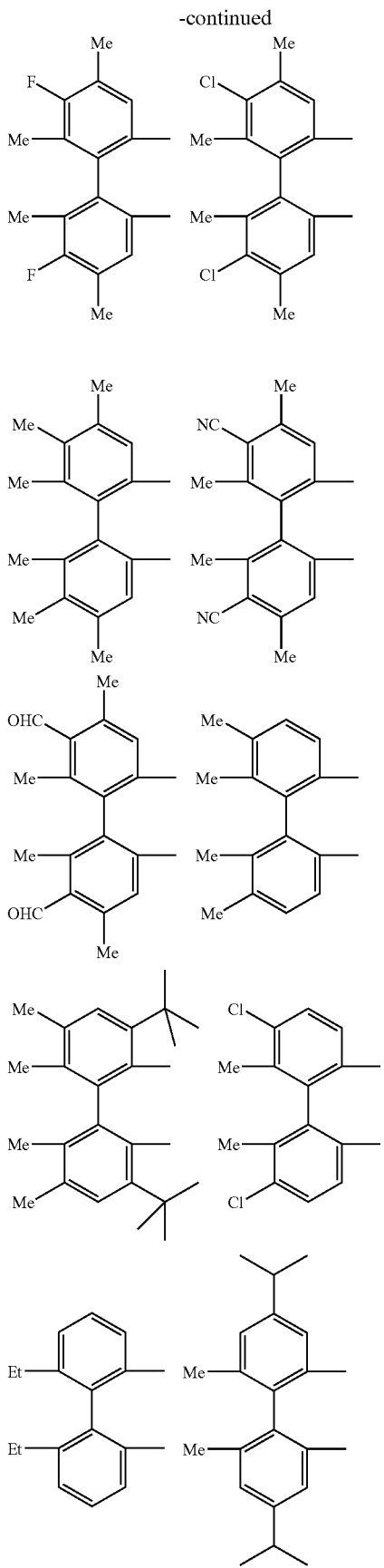
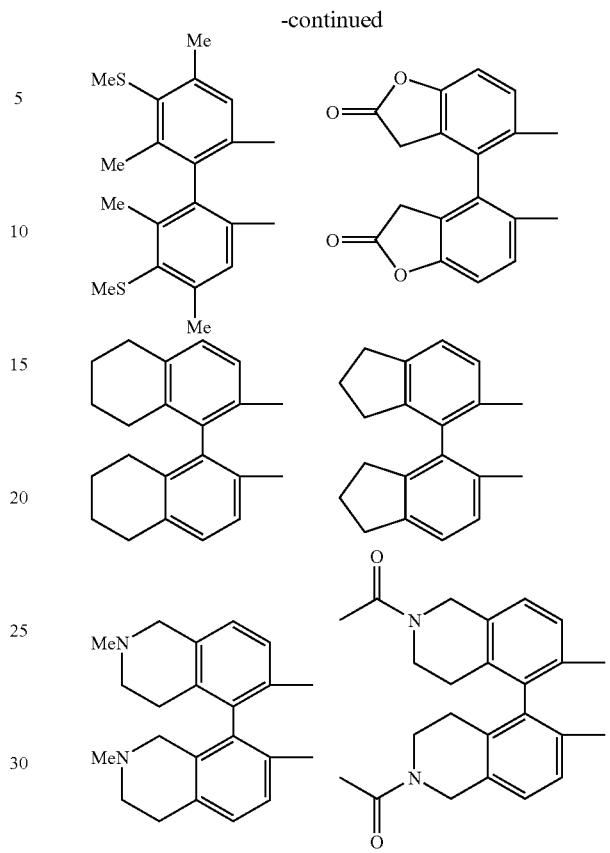

It may be pointed out at this point that any combinations of the abovementioned preferred meanings of R² with the preferred meanings of R¹ are encompassed by the invention.

The invention encompasses all stereoisomeric compounds of the chiral monophosphorus compounds of the general formula (I), both in pure form and in the form of any mixtures of stereoisomeric compounds, for example racemates or diastereomeric mixtures.

Preferred compounds of the general formula (I) are:
(S)-5,5'-dichloro-6,6'-dimethoxy-1,1'-biphenyl-2,2'-diyl isopropyl phosphite,
(R)-5,5'-dichloro-6,6'-dimethoxy-1,1'-biphenyl-2,2'-diyl isopropyl phosphite,
(R)-5,5'-dichloro-6,6'-dimethoxy-1,1'-biphenyl-2,2'-diyl (R)-1-phenylethyl phosphite,
(R)-5,5'-dichloro-6,6'-dimethoxy-1,1'-biphenyl-2,2'-diyl (S)-1-phenylethyl phosphite,
(S)-5,5'-dichloro-6,6'-dimethoxy-1,1'-biphenyl-2,2'-diyl (R)-1-phenylethyl phosphite,
(S)-5,5'-dichloro-6,6'-dimethoxy-1,1'-biphenyl-2,2'-diyl (S)-1-phenylethyl phosphite,
(S)-5,5'-dichloro-6,6'-dimethoxy-1,1'-biphenyl-2,2'-diyl cyclohexyl phosphite,
(R)-5,5'-dichloro-6,6'-dimethoxy-1,1'-biphenyl-2,2'-diyl cyclohexyl phosphite,
(S)-5,5'-dichloro-6,6'-dimethoxy-1,1'-biphenyl-2,2'-diyl phenyl phosphite,
(R)-5,5'-dichloro-6,6'-dimethoxy-1,1'-biphenyl-2,2'-diyl phenyl phosphite,
(S)-5,5'-dichloro-6,6'-dimethoxy-1,1'-biphenyl-2,2'-diyl 2,6-dimethylphenyl phosphite, (R)-5,5'-dichloro--6,6'-dimethoxy-1,1'-biphenyl-2,2'-diyl 2,6-dimethylphenyl phosphite,
(S)-5,5',6,6'-tetramethyl-3,3'-bis(tert-butyl)-1,1'-biphenyl-2,2'-diyl isopropyl phosphite,
(R)-5,5',6,6'-tetramethyl-3,3'-bis(tert-butyl)-1,1'-biphenyl-2,2'-diyl isopropyl phosphite,
(S)-5,5',6,6'-tetramethyl-3,3'-bis(tert-butyl)-1,1'-biphenyl-2,2'-diyl (rac)-1-phenylethyl phosphite,
(R)-5,5',6,6'-tetramethyl-3,3'-bis(tert-butyl)-1,1'-biphenyl-2,2'-diyl (rac)-1-phenylethyl phosphite,
(S)-5,5',6,6'-tetramethyl-3,3'-bis(tert-butyl)-1,1'-biphenyl-2,2'-diyl (S)-1-phenylethyl phosphite,
(R)-5,5',6,6'-tetramethyl-3,3'-bis(tert-butyl)-1,1'-biphenyl-2,2'-diyl (S)-1-phenylethyl phosphite,
(S)-5,5',6,6'-tetramethyl-3,3'-bis(tert-butyl)-1,1'-biphenyl-2,2'-diyl (R)-1-phenylethyl phosphite,
(R)-5,5',6,6'-tetramethyl-3,3'-bis(tert-butyl)-1,1'-biphenyl-2,2'-diyl (R)-1-phenylethyl phosphite,
(S)-5,5',6,6'-tetramethyl-3,3'-bis(tert-butyl)-1,1'-biphenyl-2,2'-diyl diphenylmethyl phosphite,
(R)-5,5',6,6'-tetramethyl-3,3'-bis(tert-butyl)-1,1'-biphenyl-2,2'-diyl diphenylmethyl phosphite,
(S)-5,5',6,6'-tetramethyl-3,3'-bis(tert-butyl)-1,1'-biphenyl-2,2'-diyl methyl phosphite,
(R)-5,5',6,6'-tetramethyl-3,3'-bis(tert-butyl)-1,1'-biphenyl-2,2'-diyl methyl phosphite,
(S)-5,5',6,6'-tetramethyl-3,3'-bis(tert-butyl)-1,1'-biphenyl-2,2'-diyl 2,6-dimethylphenyl phosphite,
(R)-5,5',6,6'-tetramethyl-3,3'-bis(tert-butyl)-1,1'-biphenyl-2,2'-diyl 2,6-dimethylphenyl phosphite,
(S)-5,5',6,6'-tetramethyl-3,3'-bis(tert-butyl)-1,1'-biphenyl-2,2'-diyl 2,6-diisopropylphenyl phosphite,
(R)-5,5',6,6'-tetramethyl-3,3'-bis(tert-butyl)-1,1'-biphenyl-2,2'-diyl 2,6-diisopropylphenyl phosphite,
(S)-5,5',6,6'-tetramethyl-3,3'-bis(tert-butyl)-1,1'-biphenyl-2,2'-diyl phenyl phosphite,
(R)-5,5',6,6'-tetramethyl-3,3'-bis(tert-butyl)-1,1'-biphenyl-2,2'-diyl phenyl phosphite,
(S)-5,5',6,6'-tetramethyl-3,3'-bis(tert-butyl)-1,1'-biphenyl-2,2'-diyl ethyl phosphite,
(R)-5,5',6,6'-tetramethyl-3,3'-bis(tert-butyl)-1,1'-biphenyl-2,2'-diyl ethyl phosphite
(S)-5,5',6,6'-tetramethyl-3,3'-bis(tert-butyl)-1,1'-biphenyl-2,2'-diyl 4-tert-butylphenyl phosphite,
(R)-5,5',6,6'-tetramethyl-3,3'-bis(tert-butyl)-1,1'-biphenyl-2,2'-diyl 4-tert-butylphenyl phosphite.

The chiral monophosphorus compounds of the invention can be prepared in a manner known per se. For example, they can be prepared by
reacting diols of the general formula (IX),

HO—R$^1$—OH  (IX)

where R$^1$ is as defined under the general formula (I), with activated phosphines of the general formula (X)

(Akt)$_n$P(R$^2$)$_{3-n}$  (X)

where
Akt is chlorine, bromine, iodine, dialkylamino such as dimethylamino or diethylamino and
R$^2$ is as defined under the general formula (I) and
n is 2 or 3,
in the presence of a base such as triethylamine or after deprotonation of the starting diol of the general formula (IX).
Akt is preferably chlorine or dimethylamino or diethylamino, particularly preferably chlorine.

If n=3, compounds of the general formula (XI)

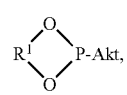

are initially formed as intermediates and these can be reacted in a further step with a compound of the general formula (XII)

H—R$^{11}$  (XII), where R$^{11}$ is a radical selected from the group consisting of substituted or unsubstituted alkoxy, substituted or unsubstituted aryloxy and secondary or tertiary amino, with these radicals being defined as under R$^1$,
either in the presence of a base such as triethylamine or after prior deprotonation to give the chiral monophosphorus compounds of the general formula (I).

The compounds of the general formula (XI) are likewise encompassed by the invention.

The separation of stereoisomers can be carried out, for example, by separating biphenyl compounds of the general formula (VI) into the enantiomers by cocrystallization with suitable chiral, enantiomerically enriched auxiliaries, for example chiral enantiomerically pure amines. The preparation of enantiomerically pure biphenols of the general formula (VI) can likewise be carried out by firstly reacting the mixture of stereomeric isomers with a suitable activated phosphorus compound such as PCl$_3$ or P(NMe$_2$)$_3$ (cf. K. Sasse, Methoden der Organischen Chemie, Houben-Weyl, Georg Thieme Verlag, 1964, Vol. XII/2, 4th edition, 5–130) and reacting this product further with an enantiomerically pure alcohol, for example menthol, to produce diastereomeric phosphites which can be separated in a customary fashion and lead after subsequent cleavage to the enantiomerically enriched biphenols of the general formula (VI). Furthermore, compounds of the formula (VI) and of the formula (I) can be separated into their enantiomers by chromatography on chiral stationary phases. Furthermore, enantiomerically pure biphenyl compounds of the formula (VI) can be obtained by reaction with enantiomerically pure biselectrophiles and substituted 2,2',6,6'-tetrahydroxy-1,1'-biphenyls using a method analogous to that of T. Harada et al. (Organic Letters, 2000, Vol. 2, p. 1319).

The invention also encompasses catalysts which comprise transition metal complexes of the novel chiral monophosphorus compounds of the general formula (I). These are, in particular, transition metal complexes of ruthenium, osmium, cobalt, rhodium, iridium, nickel, palladium, platinum and copper, preferably those of ruthenium, rhodium, iridium, nickel, palladium, platinum and copper.

As catalysts, it is possible to use, for example, either isolated transition metal complexes or transition metal complexes which are generated from the chiral monophosphorus compounds of the general formula (I) and a metal compound.

Preference is given to using transition metal complexes generated from chiral monophosphorus compounds of the general formula (I) and at least one metal compound as catalysts.

Suitable metal compounds are, by way of example and preferably, those of the general formula $$M(Y^1)_p \quad \text{(XIIIa)},$$

where
M is ruthenium, rhodium, iridium, nickel, palladium, platinum or copper and
$Y^1$ is chloride, bromide, acetate, nitrate, methanesulphonate, trifluoromethanesulphonate or acetylacetonate and
p is 3 in the case of ruthenium, rhodium and iridium, 2 in the case of nickel, palladium and platinum and 1 in the case of copper, or metal compounds of the general formula (XIIIb)

$$M(Y^2)_p B^1{}_2 \quad \text{(XIIIb)}$$

where
M is ruthenium, rhodium, iridium, nickel, palladium, platinum or copper and
$Y^2$ is chloride, bromide, acetate, methanesulphonate, trifluoromethanesulphonate, tetrafluoroborate, hexafluorophosphate perchlorate, hexafluoroantimonate, tetra(3,5-bistrifluoromethylphenyl)borate or tetraphenylborate and
p is 1 in the case of rhodium and iridium, 2 in the case of nickel, palladium, platinum and ruthenium and 1 in the case of copper,
$B^1$ are each a $C_2$–$C_{12}$-alkene such as ethylene or cyclooctene, or a nitrile such as acetonitrile, benzonitrile or benzyl nitrile, or
the $B^1{}_2$ moiety is a ($C_4$–$C_{12}$)-diene such as norbornadiene or 1,5-cyclooctadiene, or metal compounds of the general formula (XIIIc)

$$[MB^2Y^1{}_2]_2 \quad \text{(XIIIc)},$$

where
M is ruthenium and
$B^2$ is an aryl radical such as cymene, mesityl, phenyl or cyclooctadiene, norbornadiene or methylallyl, or metal compounds of the general formula (XIIId)

$$Me_p[M(Y^3)_4] \quad \text{(XIIId)},$$

where
M is palladium, nickel, iridium or rhodium and
$Y^3$ is chloride or bromide and
Me is lithium, sodium, potassium, ammonium or organic ammonium and
p is 3 in the case of rhodium and iridium and 2 in the case of nickel, palladium and platinum, or metal compounds of the general formula (XIIIe)

$$[M(B^3)_2]An \quad \text{(XIIIe)},$$

where
M is iridium or rhodium and
$B^3$ is a ($C_4$–$C_{12}$)-diene such as norbornadiene or 1,5-cyclooctadiene and
An is a noncoordinating or weakly coordinating anion such as methanesulphonate, trifluoromethanesulphonate, tetrafluoroborate, hexafluorophosphate perchlorate, hexafluoroantimonate, tetra(3,5-bistrifluoromethylphenyl)borate or tetraphenylborate.

Further suitable metal compounds are, for example, Ni(1,5-cyclooctadiene)$_2$, Pd$_2$(dibenzylideneacetone)$_3$, Pd[PPh$_3$]$_4$, cyclopentadienyl$_2$Ru, Rh(acac)(CO)$_2$, Ir(pyridine)$_2$(1,5-cyclooctadiene), Cu(phenyl)Br, Cu(phenyl)Cl, Cu(phenyl)I, Cu(PPh$_3$)$_2$Br, [Cu(CH$_3$CN)$_4$]BF$_4$ and [Cu(CH$_3$CN)$_4$]PF$_6$ or multinuclear bridged complexes such as [Rh(1,5-cyclooctadiene)Cl]$_2$ and [Rh(1,5-cyclooctadiene)Br]$_2$, [Rh(ethene)$_2$Cl]$_2$, [Rh(cyclooctene)$_2$Cl]$_2$.

Preference is given to using the following metal compounds:

[Rh(COD)Cl]$_2$, [Rh(COD)$_2$Br], [Rh(COD)$_2$]ClO$_4$, [Rh(COD)$_2$]BF$_4$, [Rh(COD)$_2$]PF$_6$, [Rh(COD)$_2$]OTf, [Rh(COD)$_2$]BAr$_4$ (Ar=3,5-bistrifluoromethylphenyl) [Rh(COD)$_2$]SbF$_6$ RuCl$_2$(COD), [(cymene)RuCl$_2$]$_2$, [(benzene)RuCl$_2$]$_2$, [(mesityl)RuCl$_2$]$_2$, [(cymene)RuBr$_2$]$_2$, [(cymene)RuI$_2$]$_2$, [(cymene)Ru(BF$_4$)$_2$]$_2$, [(cymene)Ru(PF$_6$)$_2$]$_2$, [(cymene)Ru(BAr$_4$)$_2$]$_2$, (Ar=3,5-bistrifluoromethylphenyl), [(cymene)Ru(SbF$_6$)$_2$]$_2$, [Ir(cod)$_2$Cl]$_2$, [Ir(COD)$_2$]PF$_6$, [Ir(COD)$_2$]ClO$_4$, [Ir(COD)$_2$]SbF$_6$ [Ir(COD)$_2$]BF$_4$, [Ir(COD)$_2$]OTf, [Ir(COD)$_2$]BAr$_4$ (Ar=3,5-bistrifluoromethylphenyl), RuCl$_3$, NiCl$_2$, RhCl$_3$, PdCl$_2$, PdBr$_2$, Pd(OAc)$_2$, Pd$_2$(dibenzylideneacetone)$_3$, Pd(acetylacetonate)$_2$, CuOTf, CuI, CuCl, Cu(OTf)$_2$, CuBr, CuI, CuBr$_2$, CUCl$_2$, CuI$_2$, [Rh(nbd)Cl]$_2$, [Rh(nbd)$_2$Br], [Rh(nbd)$_2$]ClO$_4$, [Rh(nbd)$_2$]BF$_4$, [Rh(nbd)$_2$]PF$_6$, [Rh(nbd)$_2$]OTf, [Rh(nbd)$_2$]BAr$_4$ (Ar=3,5-bistrifluoromethylphenyl) [Rh(nbd)$_2$]SbF$_6$ RuCl$_2$(nbd), [Ir(nbd)$_2$]PF$_6$, [Ir(nbd)$_2$]ClO$_4$, [Ir(nbd)$_2$]SbF$_6$ [Ir(nbd)$_2$]BF$_4$, [Ir(nbd)$_2$]OTf, [Ir(nbd)$_2$]BAr$_4$ (Ar=3,5-bistrifluoromethylphenyl), Ir(pyridine)$_2$(nbd), [Ru(DMSO)$_4$Cl$_2$], [Ru(CH$_3$CN)$_4$Cl$_2$], [Ru(PhCN)$_4$Cl$_2$], [Ru(COD)Cl$_2$]$_n$, [Ru(COD)(methallyl)$_2$], [Ru(acetylacetonate)$_3$]

Even greater preference is given to Rh(COD)$_2$ trifluoromethanesulphonate, Rh(nbd)$_2$PF$_6$ and Rh(nbd)$_2$BF$_4$.

The amount of metal compound used can be, for example, from 25 to 200 mol % based on the chiral monophosphorus compound of the general formula (I) which is used, preferably from 30 to 100 mol %, very particularly preferably from 40 to 60 mol % and even more preferably from 45 to 55 mol %.

The catalysts comprising transition metal complexes generated in situ or isolated transition metal complexes are suitable, in particular, for use in a process for preparing chiral compounds.

The catalysts are preferably used for asymmetric 1,4-additions, asymmetric hydroformylations, asymmetric hydrocyanations, asymmetric Heck reactions and asymmetric hydrogenations, particularly preferably asymmetric hydrogenations.

Preferred asymmetric hydrogenations are, for example, hydrogenations of prochiral C=C bonds, for example prochiral enamines, olefins, enol ethers, C=O bonds, for example prochiral ketones, and C=N bonds, for example prochiral imines. Particularly preferred asymmetric hydrogenations are hydrogenations of prochiral enamines and olefins.

The amount of metal compound used or of transition metal complex used can be, for example, from 0.001 to 5 mol % based on the substrate used, preferably from 0.001 to 0.5 mol %, very particularly preferably from 0.001 to 0.1 mol % and even more preferably from 0.001 to 0.008 mol %.

In a preferred embodiment, asymmetric hydrogenations can be carried out, for example, by generating the catalyst in situ from a metal compound and a chiral monophosphorus compound of the general formula (I) in the presence or absence of a suitable solvent, adding the substrate and placing the reaction mixture under hydrogen pressure at the reaction temperature.

As metal compounds for asymmetric hydrogenations, preference is given to using compounds of the general formula (XIIIe)

[M(B³)₂]An    (XIIIe), where

M is rhodium and

B³ is a (C₄–C₁₂)-diene such as norbornadiene or 1,5-cyclooctadiene and

An is a noncoordinating or weakly coordinating anion such as methanesulphonate, trifluoromethanesulphonate, tetrafluoroborate, hexafluorophosphate, perchlorate, hexafluoroantimonate, hexachloroantimonate, tetra (3,5-bistrifluoromethylphenyl)borate or tetraphenylborate or binuclear complexes such as [Rh(1,5-cyclooctadiene)Cl]₂ and [Rh(1,5-cyclooctadiene)Br]₂, [Rh(ethene)₂Cl]₂, [Rh(cyclooctene)₂Cl]₂.

Particularly preferred metal compounds for asymmetric hydrogenations are [Rh(1,5-cyclooctadiene)₂]BF₄, [Rh(1,5-cyclooctadiene)₂]PF₆, [Rh(norbornadiene)₂]PF₆ and [Rh(norbornadiene)₂]BF₄.

In a particularly preferred embodiment, metal compound and monophosphorus compound are dissolved in a degassed solvent in a baked-out glass autoclave. The mixture is stirred for about 5 minutes and the substrate in a degassed solvent is subsequently added. After setting the appropriate temperature, the hydrogenation is carried out under H₂ pressure.

Suitable solvents for the asymmetric hydrogenation are, for example, chlorinated alkanes such as methylene chloride, short-chain C₁–C₆-alcohols such as methanol, isopropanol or ethanol, aromatic hydrocarbons such as toluene or benzene, ketones such as acetone or carboxylic esters such as ethyl acetate.

The asymmetric hydrogenation is carried out, for example, at a temperature of from −20° C. to 200° C., preferably from 0 to 100° C. and particularly preferably from 20 to 70° C.

The hydrogen pressure can be, for example, from 0.1 to 200 bar, preferably from 0.5 to 50 bar and particularly preferably from 0.5 to 5 bar.

The catalysts of the invention are particularly suitable for processes for preparing chiral active compounds in pharmaceuticals and agrochemicals, or intermediates for these two classes.

The advantage of the present invention is that activities of far above 1 000 h⁻¹ (TOF) which have hitherto not been achieved can be achieved using ligands which are simple to prepare, in particular in asymmetric hydrogenations.

The invention is further illustrated but is not intended to be limited by the following examples in which all parts and percentages are by weight unless otherwise specified.

EXAMPLES

Example 1

Synthesis of (S)-5,5'-dichloro-6,6'-dimethoxy-1,1'-biphenyl-2,2'-dioxy)chlorophosphane

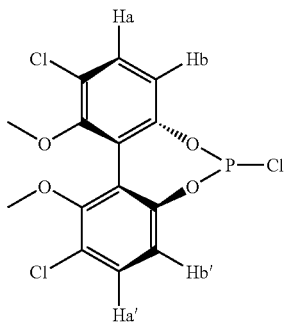

A solution of 1 g (3.17 mmol) of (S)—Cl—MeO-biphenol is added dropwise to a mixture of 0.41 ml (4.12 mmol) of PCl₃ and 0.97 ml (6.98 mmol) of NEt₃ in 5 ml of THF while cooling in ice. The mixture is stirred at RT for 1 hour, the precipitate which has formed is filtered off and is washed with a little solvent. Removal of the solvent gives the product as a yellowish oil.

¹H-NMR (CDCl₃): δ [ppm]=3.57 (s, 3H, OCH₃); 3.59 (s, 3H, OCH₃); 6.92 (d, ³J=8.7, 1H, H_{b or b'}); 7.01 (dd, 1H, ³J=8.7, J(H—P)=1.1, 1H, H_{b or b'}); 7,46 (br d, ³J=8.7, 2H, H_{a and a'}); ³¹P-NMR (CDCl₃): δ [ppm]=176.4

Examples 2–6

Synthesis of (S)-phosphites

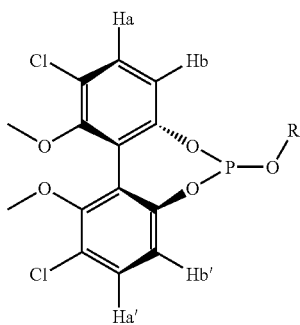

Example 2, R = i-propyl
Example 3, R = cyclohexyl
Example 4, R = (R)-1-phenylethyl
Example 5, R = phenyl
Example 6, R = 2, 6-dimethylphenyl 3.17 mmol of the appropriate alcohol (i-propanol, cyclohexanol, (R)-1-phenylethanol, phenol, 2,6-dimethylphenol) are dissolved in 5 ml of THF and admixed with 0.44 ml (3.17 mmol) of NEt₃. 1.204 g (3.17 mmol) of phosphochloridite from Example 1, dissolved in 10 ml of THF, are added dropwise at 0° C. After 1 hour, the precipitate which has formed is filtered off and is washed with a little THF.

Removal of the solvent gives the phosphites as white to slightly yellowish solids or oils.

Example 2

(S)-5,5'-Dichloro-6,6'-dimethoxy-1,1'-biphenyl-2,2'-diyl isopropyl phosphite

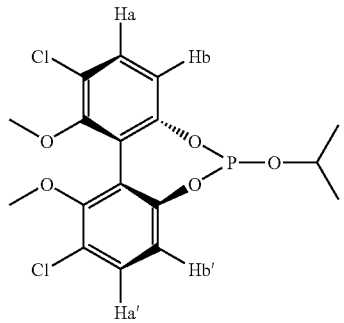

$^1$H-NMR (CDCl$_3$): δ [ppm]=1.29 (d, $^3$J=6.2, 3H, CH$_3$), 1.33 (d, $^3$J=6.2, 3H, CH$_3$); 3.53 and 3.54 (s, 3H, OCH$_3$); 4.53 (dsep, $^3$J=6.2, J(H—P)=9.0, 1H, CH); 6.83 (dd, $^3$J=8.7, J(H—P)=0.8, 1H, H$_{b\ or\ b'}$); 6.96 (dd, $^3$J=8.7, J(H—P)=1.2, 1H, H$_{b\ or\ b'}$); 7.37 (d, $^3$J=8.7, 1H, H$_{a\ or\ a'}$); 7.40 (dd, $^3$J=8.7, J(H—P)=0.5, 1H, H$_{a\ or\ a'}$); $^{31}$P-NMR (CDCl$_3$): δ [ppm]=145.3

Example 3

(S)-5,5'-Dichloro-6,6'-dimethoxy-1,1'-biphenyl-2,2'-diyl cyclohexyl phosphite

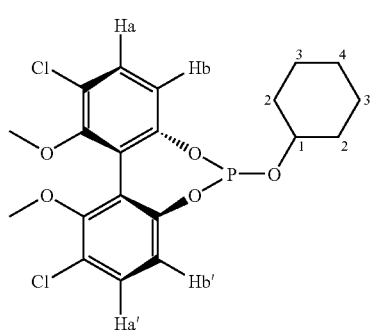

$^1$H-NMR (CDCl$_3$): δ [ppm]=1.00–2.00 (kB, 10H, CH$_2$); 3.53 and 3.54 (s, 3H, OCH$_3$); 4.19 (dsep, J=4.5, J(H—P)=9.1, 1H, CH); 6.83 (dd, $^3$J=8.7, J(H—P)=0.7, 1H, H$_{b\ or\ b'}$); 6.96 (dd, $^3$J=8.7, J(H—P)=1.1, 1H, H$_{b\ or\ b'}$); 7.36 (d, $^3$J=8.7, 1H, H$_{a\ or\ a'}$); 7.40 (d, $^3$J=8.7, 1H, H$_{a\ or\ a'}$); $^{31}$P-NMR (CDCl$_3$): δ [ppm]=146.1

Example 4

(S)-5,5'-Dichloro-6,6'-dimethoxy-1,1'-biphenyl-2,2'-diyl (R)-1-phenylethyl phosphite

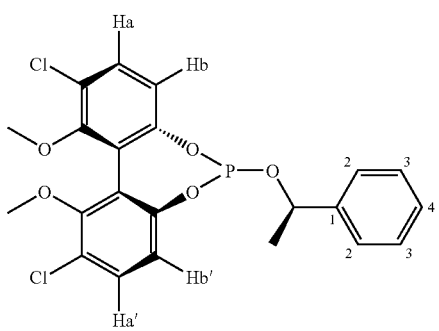

$^1$H-NMR (CDCl$_3$): δ [ppm]=1.59 (d, $^3$J=6.5, 3H, CH$_3$); 3.49 and 3.53 (s, 3H, OCH$_3$); 5.38 (dq, $^3$J=6.5, J(H—P)=9.4, 1H, CH); 6.17 (dd, $^3$J=8.7, J(H—P)=0.7, 1H, H$_{b\ or\ b'}$); 6.95 (dd, $^3$J=8.7, J(H—P)=1.1, 1H, H$_{b\ or\ b'}$); 7.21 (d, $^3$J=8.7, 1H, H$_{a\ or\ a'}$); 7.25–7.38 (kB, 5H, H$_{arom}$); 7.38 (d, $^3$J=8.7, 1H, H$_{a\ or\ a'}$); $^{31}$P-NMR (CDCl$_3$): δ [ppm]=146.9

Example 5

(S)-5,5'-Dichloro-6,6'-dimethoxy-1,1'-biphenyl-2,2'-diyl phenyl phosphite

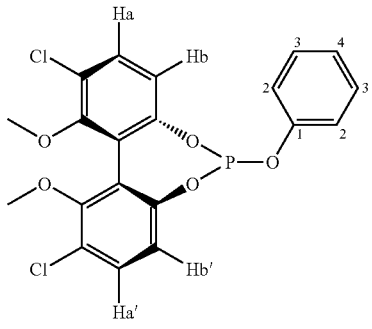

$^1$H-NMR (CDCl$_3$): δ [ppm]=3.59 and 3.61 (s, 3H, OCH$_3$); 6.90 (dd, $^3$J=8.7, J(H—P)=0.6, 1H, H$_{b\ or\ b'}$); 7.06 (dd, $^3$J=8.7, J(H—P)=1.1, 1H, H$_{b\ or\ b'}$); 7.13–7.21 (kB, 3H, H-2 and H-4); 7.32–7.38 (kB, 2H, H-3); 7.40 (d, $^3$J=8.7, 1H, H$_{a\ or\ a'}$); 7.47 (d, $^3$J=8.7, 1H, H$_{a\ or\ a'}$); $^{31}$P-NMR (CDCl$_3$): δ [ppm]=141.4

Example 6

(S)-5,5'-Dichloro-6,6'-dimethoxy-1,1'-biphenyl-2,2'-diyl 2,6-dimethylphenyl phosphite

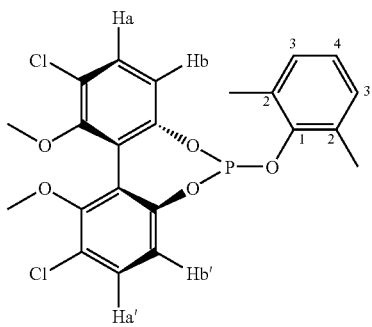

$^1$H-NMR (CDCl$_3$): δ [ppm]=2.40 (s, 6H, CH$_3$), 3.61 (s, 6H, OCH$_3$); 7.02 (dd, $^3$J=8.7, J(H—P)=1.0, 1H, H$_{b \; or \; b'}$); 7.02–7.12 (kB, 3H, H$_{arom}$); 7.03 (dd, $^3$J=8.7, J(H—P)=0.8, 1H, H$_{b \; or \; b'}$); 7.45 (d, $^3$J=8.7, 1H, H$_{a \; or \; a'}$); 7.46 (d, $^3$J=8.7, 1H, H$_{a \; or \; a'}$); $^{31}$P-NMR (CDCl$_3$): δ [ppm]=145.1

Hydrogenations

Examples 7–11

Hydrogenation of dimethyl itaconate

In a baked-out glass autoclave, 0.02 mmol of bis(norbornadiene)rhodium(I) tetrafluoroborate [Rh(nbd)$_2$]BF$_4$ and 0.04 mmol of the appropriate phosphite are dissolved in 5 ml of degassed methylene chloride. The mixture is stirred for about 5 minutes and 8 mmol of dimethyl itaconate and 0.2000 g of diglyme in 15 ml of degassed methylene chloride are subsequently added. After setting the appropriate temperature, the mixture is hydrogenated for 2 hours under a hydrogen partial pressure of 0.5 bar. Conversion and ee are determined by gas chromatography.

The results are summarized in Table 1.

TABLE 1

| | | Conversion [%] | | ee [%], configuration | |
|---|---|---|---|---|---|
| Example | Ligand (configuration) | RT | 0° C. | RT | 0° C. |
| 7 | R = i-Propyl (S) from Example 2 | 100 | 100 | 96 (S) | 97 (S) |
| 8 | R = Cyclohexyl (S) from Example 3 | 100 | 100 | 91 (S) | 94 (S) |
| 9 | R = (R)-1-Phenylethyl (S) from Example 4 | 100 | 100 | 97 (S) | 99 (S) |
| 10 | R = Phenyl (S) from Example 5 | 100 | 87 | 82 (S) | 91 (S) |
| 11 | R = 2,6-Dimethylphenyl (S) from Example 6 | 58 | 41 | 59 (S) | 74 (S) |

Example 12–13

Hydrogenation of dimethyl itaconate

In a baked-out glass autoclave, 0.02 mmol of bis(bicyclo[2.1.1]hepta-2,5-diene)rhodium(I) tetrafluoroborate [Rh(nbd)$_2$]BF$_4$ and 0.04 mmol of the appropriate phosphite are dissolved in 50 ml of degassed methylene chloride. The mixture is stirred for about 5 minutes and 200 mmol of dimethyl itaconate and 5.000 g diglyme in 250 ml of degassed methylene chloride are subsequently added. After setting the appropriate temperature, the mixture is hydrogenated for 2.5 hours under a hydrogen partial pressure of 0.5 bar. Conversion and ee are determined by gas chromatography.

The results are summarized in Table 2.

TABLE 2

| Example | Ligand (configuration) | Conversion [%] | ee [%], configuration |
|---|---|---|---|
| 12 | R = i-Propyl (S) from Example 2 | 90 | 97 (S) |
| 13 | R = (R)-1-Phenylethyl (S) from Example 4 | 100 | 99 (S) |

Example 14–18

Hydrogenation of methyl 2-acetamidoacrylate 0.0024 mmol of the appropriate phosphite are weighed out and admixed under argon with a solution of 0.0012 mmol of bis(norbornadiene)rhodium(I) hexafluorophosphate [(nbd)$_2$Rh]PF$_6$ and 0.12 mmol of methyl 2-acetamidoacrylate in 0.8 ml of degassed CH$_2$Cl$_2$. The mixture is subsequently hydrogenated for 23 hours under a hydrogen pressure of 3 bar.

The results are summarized in Table 3.

TABLE 3

| Examples | Ligand (configuration) | Conversion [%] | ee [%], configuration |
|---|---|---|---|
| 14 | R = I-Propyl (S) from Example 2 | 100 | 94 (R) |
| 15 | R = Cyclohexyl (S) from Example 3 | 100 | 94 (R) |
| 16 | R = (R)-1-Phenylethyl (S) from Example 4 | 100 | 83 (R) |
| 17 | R = Phenyl (S) from Example 5 | 100 | 77 (R) |
| 18 | R = 2,6-Dimethylphenyl (S) from Example 6 | 100 | 18 (R) |

Example 19–20

Hydrogenation of methyl cis-3-acetamidobutenoate 0.0024 mmol of the appropriate phosphite are weighed out and admixed under argon with a solution of 0.0012 mmol of bis(bicyclo[2.1.1]hepta-2,5-diene)rhodium(I) hexafluorophosphate [Rh(nbd)$_2$]BF$_4$ and 0.12 mmol of methyl cis-3-acetamidobutenoate in 0.8 ml of degassed CH$_2$Cl$_2$. The mixture is subsequently hydrogenated for 23 hours under a hydrogen pressure of 3 bar.

The results are summarized in Table 4.

TABLE 4

| Examples | Ligand (configuration) | Conversion [%] | ee [%] |
|---|---|---|---|
| 19 | R = i-Propyl (S) (Ex. 2) | 4 | 71 |
| 20 | R = Cyclohexyl (S) (Ex. 3) | 3 | 56 (other enantiomer) |

Example 21–29

Synthesis of 3,3'-bis(1,1-dimethylethyl)-5,5',6,6'-tetramethyl-1,1'-biphenyl-2,2'-diol phosphites (BIPHEN phosphites)

In a 250 ml Schlenk flask which had been baked out and flushed with argon three times, 70 ml of toluene and 1.9 ml (0.0137 mol) of triethylamine were cooled to −78° C. (dry ice/acetone). 0.3 ml (0.0034 mol) of phosphorus trichloride was added while stirring vigorously. 1 g (0.0028 mol) of solid (R)- or (S)-BIPHEN was added to this slightly turbid suspension in a countercurrent of argon over a period of 2–3 hours by means of a powder feed device. A white or yellow suspension was formed and this was warmed to room temperature overnight. The mixture was subsequently filtered through an inversion frit under protective gas and the solvent was removed under reduced pressure. This gave a yellow or white solid.

A solution of about 3 mmol (1 eq, 1.1 g) of this solid was added to 41 ml of toluene, 0.43 ml (3 mmol, 1 eq) of triethylamine and the amount of alcohol indicated in the table (Examples 21 to 29). The solution was stirred under argon overnight at room temperature. The mixture was subsequently filtered through an inversion frit to remove the ammonium salt and the solvent was removed under reduced pressure. This gave a yellow or white solid.

The yields and physical data are summarized in Table 5.

TABLE 5

| Example: | Amount of alcohol | Yield | Analysis |
|---|---|---|---|
| 21 | 0.26 g (0.0028 mol) of phenol | 0.911 g (68%) of yellow solid | $^{31}$P NMR: δ = 135.29 ppm |
| 22 | 0.15 ml (0.0028 mol; 1 eq) of ethanol | 0.802 g (67%) of white solid | $^{31}$P NMR: δ = 132.45 ppm |
| 23[1] | 0.34 g (0.0028 mol; 1 eq) of 2,6-dimethylphenol 0.14 g (0.0058 mol; 1, 1 eq) of sodium hydride | 1.353 g (95%) of white solid | $^{31}$P NMR: δ = 135.77 ppm |
| 24 | 0.11 ml (0.0028 mol; 1 eq) of methanol | 1.151 g (99%) of white solid | $^{31}$P NMR δ = 130.18 ppm |
| 25 | 0.424 ml (0.0028 mol; 1 eq) of tert-butylphenol | 0.978 g (65%) of yellow solid | $^{31}$P NMR δ = 136.3 ppm |
| 26 | 0.34 ml (0.0028 mol; 1 eq) of phenylethyl alcohol | 0.881 g (62%) of whitish yellow solid | $^{31}$P NMR δ = 141.82 ppm and 138.58 (diastereomeric pair) |
| 27 | 0.52 g (0.0028 mol; 1 eq) of diphenyl carbinol | 0.771 g (48%) of white solid | $^{31}$P NMR δ = 136.35 ppm |
| 28 | 0.22 ml (0.0028 mol; 1 eq) of isopropanol | 0.521 g (33%) of white solid | $^{31}$P NMR: δ 142.84 ppm |
| 29[1] | Five-fold batch using 8.1 ml (0.014 mol; 1 eq) of 2,6-diisopropylphenol | 7.23 g (92%) of yellow solid | $^{31}$P NMR: δ 1365.74 ppm |

[1] Additional use of sodium hydride as base to form the phenoxide

Examples 30 to 33

Asymmetric Hydrogenation Using BIPHEN Phosphites

The ligands (from Examples 21 and 24) were weighed into the reaction vessels (batch size: 0.09 mmol). The substrates were subsequently each prepared as a stock solution (dilution: 0.13 mol/l) in 5.1 ml of methylene chloride and degassed. 5.6 mg of bis-(1,5-cyclooctadiene) rhodium triflate Rh(COD)$_2$OTf were in each case added and the mixture was degassed again. In a glove box, 0.72 ml of solution was placed in each of the individual vessels (2 mol % of catalyst and 2 mol % of ligand). All batches were hydrogenated in an autoclave (23 h, 3 bar of hydrogen pressure, RT).

The results are summarized in Tables 6 and 7.

TABLE 6

Hydrogenation of methyl cis-3-acetamidobutenoate

| Ligand | 21 | 24 |
|---|---|---|
| Conversion [%] | 100 | 100 |
| ee [%] | 11.3 | 59 |
| Example No. | 30 | 31 |

TABLE 7

Hydrogenation of dimethyl itaconate

| Ligand | 21 | 24 |
|---|---|---|
| Conversion [%] | 100 | 100 |
| ee [%] | 14 | 13 |
| Example No. | 32 | 33 |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. Chiral monophosphorus compounds selected from the group consisting of
   (S)-5,5'-Dichloro-6,6'-dimethoxy-1,1'-biphenyl-2,2'-diyl isopropyl phosphite,
   (R)-5,5'-dichloro-6,6'-dimethoxy-1,1'-biphenyl-2,2'-diyl isopropyl phosphite,
   (R)-5,5'-dichloro-6,6'-dimethoxy-1,1'-biphenyl-2,2'-diyl (R)-1-phenylethyl phosphite,
   (R)-5,5'-dichloro-6,6'-dimethoxy-1,1'-biphenyl-2,2'-diyl (S)-1-phenylethyl phosphite, (S)-5,5'-dichloro-6,6'-dimethoxy-1,1'-biphenyl-2,2'-diyl (R)-1-phenylethyl phosphite,
(S)-5,5'-dichloro-6,6'-dimethoxy-1,1'-biphenyl-2,2'-diyl (S)-1-phenylethyl phosphite,
(S)-5,5'-dichloro-6,6'-dimethoxy-1,1'-biphenyl-2,2'-diyl cyclohexyl phosphite,
(R)-5,5'-dichloro-6,6'-dimethoxy-1,1'-biphenyl-2,2'-diyl cyclohexyl phosphite,
(S)-5,5'-dichloro-6,6'-dimethoxy-1,1'-biphenyl-2,2'-diyl phenyl phosphite,
(R)-5,5'-dichloro-6,6'-dimethoxy-1,1'-biphenyl-2,2'-diyl phenyl phosphite,
(S)-5,5'-dichloro-6,6'-dimethoxy-1,1'-biphenyl-2,2'-diyl 2,6-dimethylphenyl phosphite,
(R)-5,5'-dichloro-6,6'-dimethoxy-1,1'-biphenyl-2,2'-diyl 2,6-dimethylphenyl phosphite,
(S)-5,5',6,6'-tetramethyl-3,3'-bis(tert-butyl)-1,1'-biphenyl-2,2'-diyl isopropyl phosphite,
(R)-5,5',6,6'-tetramethyl-3,3'-bis(tert-butyl)-1,1'-biphenyl-2,2'-diyl isopropyl phosphite,
(S)-5,5',6,6'-tetramethyl-3,3'-bis(tert-butyl)-1,1'-biphenyl-2,2'-diyl (rac)-1-phenylethyl phosphite,
(R)-5,5',6,6'-tetramethyl-3,3'-bis(tert-butyl)-1,1'-biphenyl-2,2'-diyl (rac)-1-phenylethyl phosphite,
(S)-5,5',6,6'-tetramethyl-3,3'-bis(tert-butyl)-1,1'-biphenyl-2,2'-diyl (S)-1-phenylethyl phosphite,
(R)-5,5',6,6'-tetramethyl-3,3'-bis(tert-butyl)-1,1'-biphenyl-2,2'-diyl (S)-1-phenylethyl phosphite,
(S)-5,5',6,6'-tetramethyl-3,3'-bis(tert-butyl)-1,1'-biphenyl-2,2'-diyl (R)-1-phenylethyl phosphite,
(R)-5,5',6,6'-tetramethyl-3,3'-bis(tert-butyl)-1,1'-biphenyl-2,2'-diyl (R)-1-phenylethyl phosphite,
(S)-5,5',6,6'-tetramethyl-3,3'-bis(tert-butyl)-1,1'-biphenyl-2,2'-diyl diphenylmethyl phosphite,
(R)-5,5',6,6'-tetramethyl-3,3'-bis(tert-butyl)-1,1'-biphenyl-2,2'-diyl diphenylmethyl phosphite,
(S)-5,5',6,6'-tetramethyl-3,3'-bis(tert-butyl)-1,1'-biphenyl-2,2'-diyl methyl phosphite,
(R)-5,5',6,6'-tetramethyl-3,3'-bis(tert-butyl)-1,1-biphenyl-2,2'-diyl methyl phosphite,
(S)-5,5',6,6'-tetramethyl-3,3'-bis(tert-butyl)-1,1'-biphenyl-2,2-diyl 2,6-di-methylphenyl phosphite,
(R)-5,5',6,6'-tetramethyl-3,3'-bis(tert-butyl)-1,1'-biphenyl-2,2'-diyl 2,6-di-methylphenyl phosphite,
(S)-5,5',6,6'-tetramethyl-3,3'-bis(tert-butyl)-1,1'-biphenyl-2,2'-diyl 2,6-di-isopropylphenyl phosphite,
(R)-5,5',6,6'-tetramethyl-3,3'-bis(tert-butyl)-1,1'-biphenyl-2,2'-diyl 2,6-di-isopropylphenyl phosphite,
(S)-5,5',6,6'-tetramethyl-3,3'-bis(tert-butyl)-1,1'-biphenyl-2,2'-diyl phenyl phosphite,
(R)-5,5',6,6'-tetramethyl-3,3'-bis(tert-butyl)-1,1'-biphenyl-2,2'-diyl phenyl phosphite,
(S)-5,5',6,6'-tetramethyl-3,3'-bis(tert-butyl)-1,1'-biphenyl-2,2'-diyl ethyl phosphite,
(R)-5,5',6,6'-tetramethyl-3,3'-bis(tert-butyl)-1,1'-biphenyl-2,2'-diyl ethyl phosphite
(S)-5,5',6,6'-tetramethyl-3,3'-bis(tert-butyl)-1,1'-biphenyl-2,2'-diyl 4-tert-butylphenyl phosphite and
(R)-5,5',6,6'-tetramethyl-3,3'-bis(tert-butyl)-1,1'-biphenyl-2,2'-diyl 4-tert-butylphenyl phosphite, butylphenyl phosphite.

* * * * *